United States Patent [19]
Furth et al.

[11] Patent Number: 5,998,382
[45] Date of Patent: *Dec. 7, 1999

[54] TARGETING GENE EXPRESSION TO LIVING TISSUE USING JET INJECTION

[75] Inventors: Priscilla Anne Furth; Lothar Hennighausen, both of Chevy Chase, Md.

[73] Assignee: The United States of America as represented by the Department of Health and Human Services, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/433,265

[22] Filed: May 2, 1995

Related U.S. Application Data

[63] Continuation of application No. 07/886,204, May 21, 1992, abandoned.

[51] Int. Cl.⁶ .................................................. A01N 43/04
[52] U.S. Cl. ............................................................ 514/44
[58] Field of Search ......................... 514/44; 435/172.3, 435/320.1, 325, 6, 375, 377, 455, 459, 470; 935/52, 54–58, 76, 77

[56] References Cited

U.S. PATENT DOCUMENTS

| | | | |
|---|---|---|---|
| 3,805,783 | 4/1974 | Ismach | 604/71 |
| 3,908,651 | 9/1975 | Fudge | 604/71 |
| 4,333,922 | 6/1982 | Herschler | 424/184.1 |
| 4,458,630 | 7/1984 | Sharma et al. | 119/6.8 |
| 4,689,402 | 8/1987 | Sekine et al. | 530/399 |
| 5,041,244 | 8/1991 | Baron | 252/589 |
| 5,080,648 | 1/1992 | D'Antonio | 604/72 |

FOREIGN PATENT DOCUMENTS

| | | |
|---|---|---|
| 0 405 696 | 1/1991 | European Pat. Off. . |
| 0 414 044 | 2/1991 | European Pat. Off. . |
| WO 91/00915 | 1/1991 | WIPO . |

OTHER PUBLICATIONS

Furth, P.A. et al. "Gene Transfer into Somatic Tissues by Jet Injection", *Analytical Biochemistry*, 205 (1992):365–368.
Sautter, C. et al. "Micro–Targeting: High Efficiency Gene Transfer Using a Novel Approach for the Acceleration of Micro–Projectiles", *Bio/Technology*, 9 (1991):1080–1085.
Buhler et al. Biotechnology, vol. 8 (1990) pp. 140–143.
Romanczuk et al. J. Virology, vol. 64 (#6) (1990) pp. 2849–2859.
Wolff et al. Science, vol. 247 (1990) pp. 1465–1468.
Craigie et al. Cell, vol. 62 (1990) pp. 829–837.
Watson et al. N.A.R., vol. 12 (#13) (1984), pp. 5145–5164.
Stillman et al. Bioessays, vol. 9 (#2 & 3) (1988) pp. 56–60.
Pittius, C., et al. P.N.A.S., vol. 85 (1988) pp. 5874–5878.
Benvenisty et al. P.N.A.S., vol. 83 (1986) pp. 9551–9555.
D. Brown, Washington Post, Dec. 8, 1995 pp. A1 & A22.
A. Coghlan et al. New Scientist, Nov. 25, 1995, pp. 14–15.
S. Orkin et al. NIH Gene Therapy Report, Dec. 7, 1995.
J. Ulwer et al. Science 259:1745–9 (1993).
M. Boshant et al. Cell 41:521–30 '85.
C. Gorman et al. MolCell. Biol. 2(9) :1044–51 '82.
F. Ausubel et al. Curr. Periods in Mol. Biol., vol. 1, John Wiley & Sons, '94–'96, p. 9.0.6.
T. Friedman, Sci. Amer. Jun. '97 pp. 96–101.
I. Verma et al. Nature 389:239–42 '97.
Nicolau, Claude, et al. "In vivo expression of rat insulin after intravenous administration of the liposome–entrapped gene for rat insulin I", *Proc. Natl. Acad. Sci, USA,* vol. 80, (Feb. 1983) pp. 1068–1072.
Seeger, Christoph, et al. "The cloned genome of ground squirrel hepatitis virus is infectious in the animal", *Proc. Natl. Acad. Sci, USA,* vol. 81, (Sep. 1983) pp. 5849–5852.
Dubensky, Thomas W. et al. "Direct transfection of viral and plasmid DNA into the liver or spleen of mice", *Proc. Natl. Acad. Sci, USA,* vol. 81, (Dec. 1984) pp. 7529–7533.
Wu, George Y. et al. "Receptor–mediated Gene Delivery and Expression in vivo", *J. Biol. Chem.,* vol. 263, No. 29, (Oct. 15, 1988) pp. 14621–14624.
Kaneda, Yasufumi, et al. "Increased Expression of DNA Cointroduced with Nuclear Protein in Adult Rat Liver", *Science,* vol. 243, (Jan. 20, 1989) pp. 375–378.
Friedman, Theodore. "Progress Toward Human Gene Therapy", *Science,* vol. 244, (Jun. 16, 1989) pp. 1275–1281.
Yang, Ning–Sun "In vivo and in vitro gene transfer to mammalian somatic cells by particle bombardment", *Proc. Natl. Acad. Sci., USA,* vol. 87, (Dec. 1990) pp. 9568–9572.
Niwa, Hitoshi, et al. "Efficient Selection for High–expression transfectants with a novel eukaryotic vector", *Gene,* vol. 108, (1991) pp. 192–200.
Brandsma, Janet L. et al. "Use of a rapid, efficient inoculation method to induce papillomas by cottontail rabbit papillomavirus DNA shows that the E7 gene is required", *Proc. Natl. Acad. Sci., USA,* vol. 88, (Jun. 1991) pp. 4816–4820.
Klein, Theodore M. et al. "Transformation of Microbes, Plants and Animals by Particle Bombardment", *Bio/Technology,* vol. 10, (Mar. 1992) pp. 286–291.
Tang, De–chu, et al. "Genetic immunization is a simple method for eliciting an immune response", *Nature,* vol. 356, (Mar. 12, 1992), pp. 152–154.

*Primary Examiner*—James Martinell
*Attorney, Agent, or Firm*—Fish & Richardson P.C.

[57] ABSTRACT

The present invention provides a method of targeting transient gene expression and stable gene expression from the exogenous administration of a DNA sequence, which sequence is less than a complete genome, wherein said DNA sequence encodes RNA and protein, or RNA only, to differentiate tissue of living organisms wherein said DNA sequence through a jet injector technique, and said DNA sequence of less than a complete genome is expressed in a living organism. The present invention further provides a flexible multi-nozzle injector device with a wide surface area to allow molding of the injector nozzle to the surface contours of the tissue. Another aspect of the present invention provides an injection device having a long nozzle for injection of DNA deep into the host tissue. Also, in a further aspect the present invention provides an injector device modified to be used with and/or inject through an endoscopic device.

12 Claims, 2 Drawing Sheets

TARGETING GENE EXPRESSION TO LIVING TISSUE USING JET INJECTION

This application is a continuation of application Ser. No. 07/886,204 filed May 21, 1992, now abandoned.

FIELD OF THE INVENTION

The present patent application involves the introduction of DNA sequences encoding RNA and proteins into the differentiated tissues of a living organism. It involves a procedure by which DNA sequences can be targeted to differentiated an undifferentiated tissue and for enhancing the expression of DNA sequences in specific target cells.

BACKGROUND OF THE INVENTION

It is known in this field that a full length cottontail rabbit papillomavirus (CRPV) DNA genome of the Washington B strain of the virus can be injected into rabbit skin as an episome by several methods (See, Brandsma et al, Proc. Natl. Acad. Sci., U.S.A., Vol. 88, pages 4816–4820 (June 1991)). In the Brandsma publication, inter alia, the authors discuss, as one of the several methods of inoculating with the episome, the use of a ped-o-jet (a standard hypodermic jet injector gun) for injecting the entire viral genome of the cottontail rabbit papillomavirus (CRPV) DNA into rabbit skin. Prior to injection of the full length genome Brandsma purifies it either by using standard cesium chloride centrifugation or by using polyethylene glycol precipitation followed by proteinase K digestion. Equivalent purification results were obtained with DNA purified by either method.

The Brandsma publication alludes to the possibility that further research might lead to other forms of DNA that might also be injected using the jet injection technique, but there is no data or descriptional basis to lead one to expect any likelihood of success with injecting DNA if less than a complete genome episome.

The four different methods discussed in Brandsma et al for inoculating rabbit skin involved (a) epithelial scarification with a razor blade followed by smearing on of DNA, (b) scratching the skin with the back of an 18-gauge needle followed by smearing on of DNA, (c) intradermal inoculation and puncture 200 times with a 27-gauge needle, and (d) interdermal inoculation using a PED-O-Jet injector (Stirn Industries, Dayton, N.J.).

The four types of inoculations were performed on four to five pound random-bred New Zealand white female rabbits, anesthetized with ketamine hydrochloride (44 milligrams per kilogram) after clipping their backs free of hair. The inoculant contained 70 micrograms of supercoiled CRPV-p LAI1 DNA (wild type or mutant) per site in 0.1 milliliter of 0.15 M NaCl or 10 mM Tris.HCl/1 mM EDTA.

Inoculation methods (a) and (b) were not very efficient, but the intradermal inoculation and puncture (manual) and the jet injector methods both induced papillomas. The intradermal manual method induced papillomas in 15–25% of the inoculated sites on all the rabbits. The jet-injector caused 23–81% of the inoculated sites to form papillomas.

The Brandsma paper concluded that there was some advantage as to the total number of papillomas produced and a savings of time for the inoculation. However, it was not clear whether the increased rate of producing papillomas from the DNA episomes could also be accounted for possibly of different depths at which the injection was done into the tissue using the manual or the jet method. Further, there is no data for the manual method using a larger diameter (smaller gauge) needle for the injection. The 27 gauge needle used has a very small diameter and could possibly have broken the episome DNA into fragments.

In other words, Brandsma is not clear as to whether the jet injector and the manual injection were done at the same depth in the tissue. Possibly, one of the two methods injected deeper into the tissue or injected over a wider area of tissue. Specifically a different manual injection technique (such as injecting while withdrawing the needle instead of at just one depth) may have been much more successful than the technique used by Brandsma. Thus, the data produced in Brandsma is inconclusive on this point.

Moreover, in Brandsma there is no experimental evidence or data that would provide any reasonable basis for believing that DNA fragments which are not capable of producing an episome would be expressed if they were injected either manually or using the jet injection.

Accordingly, there is a need in this art for an improved method for initiating gene expression for DNA which corresponds to less than a complete genome, i.e., gene fragments, in a host and for improved equipment with which to perform these injections.

SUMMARY OF THE INVENTION

It is an object of the present invention to provide a method of targeting transient gene expression and stable gene expression from the exogenous administration of a DNA sequence, which sequence is less than a complete genome, wherein said DNA sequence encodes RNA and protein, or RNA only, to differentiate tissue of living organisms wherein said DNA sequence through a jet injector technique, and said DNA sequence of less than a complete genome is expressed in a living organism.

Another object of the present invention is to provide a flexible multi-nozzle injector device with a wide surface area to allow molding of the injector nozzle to the surface contours of the tissue.

Still another object of the present invention is to provide an injection device having a long nozzle for injection of DNA deep into the host tissue.

It is a further object of the present invention to provide an injector device modified to be used with and/or injected through an endoscopic device.

DETAILED DESCRIPTION OF THE INVENTION

The present invention provides a method of targeting transient gene expression and stable gene expression from the exogenous administration of a DNA sequence of less than a complete genome, wherein said DNA sequence encodes RNA and protein, or RNA only, to differentiate tissue of living organisms, wherein said DNA sequence is administered through a jet injector technique and said sequence of less than a complete genome is expressed in a living organism.

In another aspect the present invention relates to a flexible multi-nozzle injector with a wide surface area to allow for molding of the injector nozzle through the surface of the tissue. In another aspect of the invention, the invention relates to an injector with a long injection port for injecting deep into tissue in a regulated fashion. A still further aspect of the present invention is an injector with an injector nozzle having an injector port which has been modified to use with an endoscope.

The improved jet injection device for injection of the human female cervix consists of a jet injection nozzle which is small enough to position on the human female cervix (which is located within the vagina). The nozzle is located at the end of a length of injection tubing sufficient to position the injection nozzle on the surface of the cervix, with the jet propulsion system located outside the body. The device is held in position at the cervix by cervical clamps. The nozzle is moved over the entire surface of the cervix by moving a platform which is located outside the body. The movements of the platform are controlled by computer to insure that small movements will be made (approximately four millimeter is optimal) and the entire cervical surface is covered with injections. As an alternative, a manually driven device can be substituted for the computer.

The improved jet injection device for injection of living tissue using an endoscopic device may be used in endoscopy, bronchoscopy, cystoscopy, colonoscopy, laparoscope, or other similar procedures using a type of endoscopic device. The endoscopic injection device is coupled to conventional endoscopic technology. The endoscope is used to visualize the tissue to be injected and to position the jet injection device at that sight. The jet injection nozzle and tubing is made small enough to enter the appropriate body orifice for each individual endoscopic device.

Figure 3:
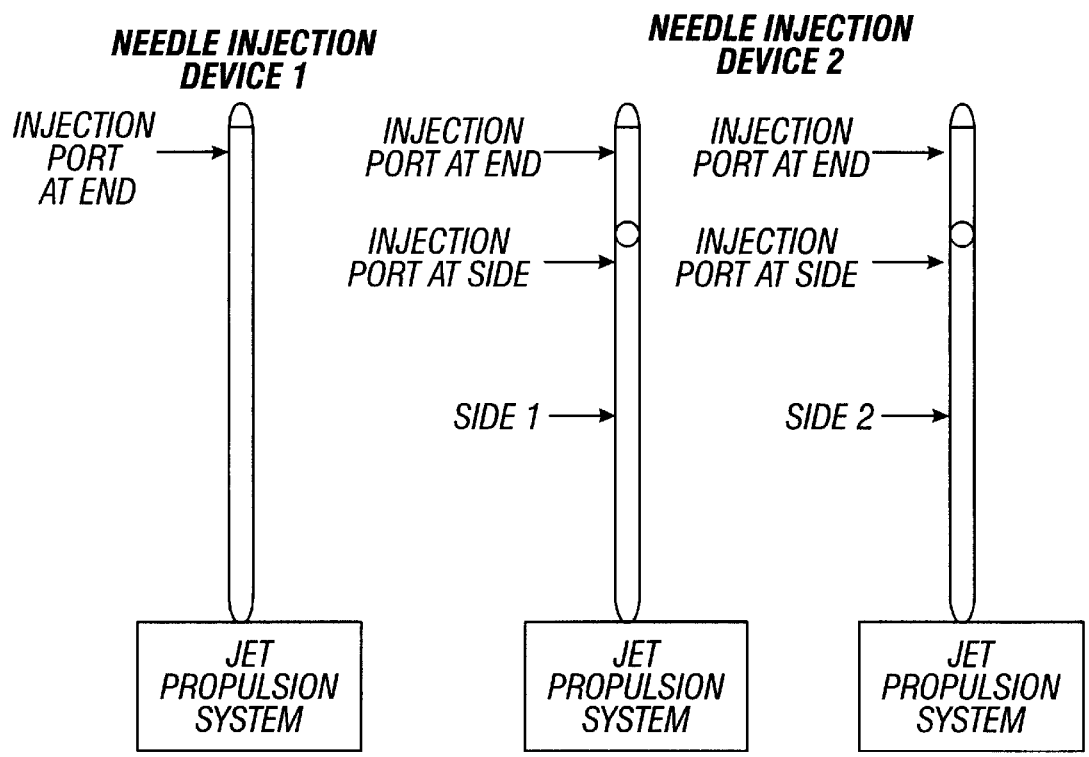
FIG. 3 is a diagram showing an improved jet injection nozzle for the deep injection of DNA into tissues.

The improved jet injection nozzle for deep injection of tissue are designed to be able to deliver a jet injection to a tissue internally. The needle injection device is inserted into a tissue at the required depth. The injection is then performed. Two types of needle injections can be used. A first type of device delivers the injection through a single port. A second type of device delivers the injection through multiple ports, i.e. two or more injection ports. The diagram in FIG. 3 shows one port at the end of the needle and one port on each side. Additional ports may be added as needed for particular tissues. The diameter of the needle is varied for each type of tissue, usually between 12 and 18 gauge, which is a large diameter needle.

The method according to the invention preferably involves the steps of a member selected from the group consisting of (a) ablation of malignant cells, (b) ablation of cells infected with specific viruses, (c) gene therapy, (d) immunization, (e) generation of transgenic organisms, (f) converting secretory cells of living organisms into bioreactors for producing a protein, (g) modifying the expression of indigenous gene, (h) providing a means for studying the effects of specific proteins in differentiated and undifferentiated tissue, (i) generating an animal model system for human diseases, and (j) inducing wound healing via the production of specific growth factor genes.

Further preferred is a method wherein the secretory cells of the living organism are mammary or bladder cells.

Another preferred aspect of the invention is a method according to wherein the exogenous DNA sequence is a DNA sequence selected from the group consisting of a DNA sequence having enhancer/promotor and other regulatory elements, a DNA sequence which can be transcribed into an RNA which RNA can be (a) translated into a protein, (b) includes a transcriptional termination signal, and (c) may encode a signal peptide which allows a protein to be exported from the cell, a DNA sequence which targets a gene for incorporation into the genome, a DNA sequence which directly replicates in eukaryotic cells, and a plasmic sequence which allows DNA replication in prokaryotic cells.

The preferred exogenous DNA sequences are DNA sequences which naturally occur in a genome but are not a complete genome, or a DNA sequence which is constructed using enhancer/promoter components, termination signals, and may include a signal peptide coding sequences from different genes which are combined to directly express in a specific manner. Even more preferred is a method wherein the enhancer/promotor sequence is a naturally occurring element such as the HCMVIE1 promotor/enhancer, or the enhancer/promotor sequences constructed using specific DNA elements which mediate binding by specific transcription factors to directly express only in specific cell types. A preferred synthetic promoter is composed of a generic TATA box and binding cites for the E2 transcription factor and coded by the papillomavirus genome, wherein the gene expression from such a promotor is confined to cells expressing the E2 protein from papillomavirus.

The development of techniques to transfect DNA into somatic tissues is motivated by the potential value of this technology for gene therapy; (Friedmann, T. (1989) *Science* 244, 1275–1281) and for genetic immunization; (Tang, D., DeVit, M., and Johnston, S. A. (1992) *Nature* 356, 152–154). Techniques that have been described include needle injection of DNA in a 5% sucrose solution; (Wolff, J. A., Malone, R. W., Williams, Chong, W., Acsadi, G., Jani, A., and Felgner, P. L. (1990) *Science* 247, 1465–1468) or following co-precipitation with $CaCl_2$; (Benvenisty, N., and Reshef, (1986) *Proc. Natl. Acad. Sci. USA* 81, 5849–5852; Nabel, E. G., Plautz, G., and Nabel, G. J. (1990) *Science* 249, 1285–1288; and Seeger, C., Ganem, D., and Varmus, H. E. (1984) *Proc. Natl. Acad. Sci. USA* 81, 5849–5852) encased in liposomes; (Nabel, E. G., Plautz, G., and Nabel, G. J. (1990) *Science* 249, 1285–1288 and Nicolau, C., Le Pape, A., Soriano, P., Fargette, F., and Juhel, M-F 1983 *Proc. Natl. Acad. Sci. USA* 80, 1068–1072) in combination with nuclear proteins; (Kenaeda, Y., Iwai, K., and Uchida, T. (1989) *Science* 243, 375–378) or another carrier; (Wu, G. Y., and Wu, C. H. (1988) *J. Biol. Chem.* 263, 14621–14624). Somatic cells have also been transformed by particle bombardment; (Zelenin, A. V., Alimov, A. A., Titomirov, A. V., Kazansky, A. V. et al (1991) *FEBS Lett.* 280, 94–96; Yang, N.-S., Burkholder, J., Roberts, B., Martinell, B., and McCabe, D. (1990) *Proc. Natl. Acad. Sci. USA* 87, 9568–9572 and Klein, T. M., Arentzen, R., Lewis, P. A., and Fitzpatrick-McElligott, S. (1992) *BIO/TECHNOLOGY* 10, 286–291) or using retroviral vectors; (Friedmann, T. (1989) *Science* 244, 1275–1281). The entire cottontail rabbit papillomavirus (CRPV) genome has been jet injected by an air pressure propulsion system into rabbit epithelium as discussed above; (Brandsma, J., Yang, Z.-H., Barthold, S. W., and Johnson, E. A. (1991) *Proc. Natl. Acad. Sci. USA* 88, 4816–4820).

Surprisingly, the present Applicants have found that corresponding genes to less than a complete genome can be expressed by jet injection of reporter genes through the skin surface to transfect skin, muscle, fat, and mammary tissue of living animals. Further, Applicants have discovered that the isolated mouse mammary gland can be successfully transfected by this technique.

The present invention will be more clear by the following specific application of its concepts.

Expression Vectors

Three hybrid genes were used. The first contained human cytomegalovirus immediate early gene 1 (HCMVIE1) enhancer/promoter sequences and the bacterial chloramphenicol acetyl transferase (CAT) gene. This hybrid gene is expressed in at least 28 different mouse tissues and it is also active in a wide variety of tissue culture cell lines; (Furth, P. A., Hennighausen, L., Baker, C., Beatty, B., and Woychik, R. (1991) *Nuc. Acids Res.* 19, 6205–6208). The second vector contained whey acidic protein (WAP) promoter sequences between −450 and +24 and the CAT gene. In contrast to the universally expressed HCMVIE1 enhancer/promoter, the WAP promoter is active only in differentiated mammary tissue; (Pittius, C., Hennighausen, L., Lee, E., Westphal, H., Nicoli, E., Vitale, J., and Gordon, K. (1988) *Proc. Natl. Acad. Sci. USA* 85, 5874–587816). The third expression vector contained HCMVIE1 enhancer/promoter sequences and the bacterial β-galactosidase gene (CLONTECH Laboratories, Inc., Palo Alto, Calif.).

Animals

Four male and 15 female C57B6/SJL mice between 15 to 24 weeks of age were injected with gene constructs in this study. Females were mated and injected 10 to 15 days after copulation. Pregnancy was confirmed at the time of autopsy. Mammary glands of four Rambouillet ewes, near the end of lactation (5 to 7 weeks after parturition) were also injected. All animals were observed for morbidity from jet injection. The injected tissues were examined for evidence of tissue damage at the time of autopsy or biopsy.

Jet Injection of DNA

Supercoiled DNA fragments at 1 μg/μl in 1 mM TRIS-.1 mM EDTA were introduced into specific tissues with a Ped-O-Jet injection (Stirn Industries, Dayton, N.J.). Each mouse was anesthetized with 0.7 ml 0.175% 2,2,2,-tribromoethanol in 3.5% 3° amyl alcohol (Avertin) and the site(s) of injection were lightly shaved with a razor.

The injector was placed on the skin surface and fired. Between one and three injections were made at the surface of the skin overlying the inguinal mammary glands and the thigh muscle. One to three injections in volumes of 100 μl or 300 μl per injection were made at each site. In some cases the inguinal mammary glands were removed immediately after injection and cultured.

In other experiments the inguinal mammary glands were first excised and placed in a petri dish, injected and subsequently cultured. The injector was placed at or just above the surface of the mammary glands and each gland was injected five times with a volume of 100 μl.

Because it was not known if jet injected solutions would penetrate the skin overlying sheep mammary glands, three sites of injection were tested during the initial experiment in sheep. Injections were performed on the skin surface, into subcutaneous fat and at the surface of the fascia surrounding the mammary gland. Between one and three injections were made at each site. Volumes of the injection ranged from 100 μl to 500 μl. In subsequent sheep experiments injections were performed at the skin surface. In two cases biopsies of the sheep gland were removed immediately after injection and cultured.

Mammary Gland Explant Cultures

Mammary tissue was transferred into medium M-199 containing 100 U/ml penicillin, 100 μg/ml streptomycin and 0.25 μg/ml Fungizone and 1 μg/ml insulin. Explant cultures were prepared as previously described; (Shamay, A., Zeelon, E., Ghez, Z., Cohen, N., Mackinlay, A. G. and Gertler, A. (1987) *J Endocrinol.* 113, 81–88) and cultured at 37° C. in medium supplemented with insulin (1 μg/ml), cortisol (0.5 μg/ml), and prolactin (1 μg/ml). The media was changed every 24 hours.

Analysis of Chloramphenicol Acetyl Transferase (CAT) Activity

Mice were killed by cervical dislocation 48 hours after injection, and targeted tissues were removed. Cultured mouse and sheep mammary glands were harvested after 48 hours in culture. In two cases the injected sheep tissues were harvested 24 or 48 hours after injection by excisional biopsy following local lidocaine anesthesia. In three cases the sheep tissues were harvested 48 hours after injection during autopsy. The three sheep were killed by stunning them with a captive bolt followed by exsanguination. Protein extracts were prepared, concentration of protein determined and CAT assays performed as previously described; (Leonard, J. M., Khillan, J. S., Gendelman, H. E., Adachi, A., Lorenzo, S. J., Westphal, H., Martin, M., and Meltzer, M. S. (1989) *AIDS Res. Hum. Retroviruses* 5, 421–430). The acetylated and nonacetylated forms of chloramphenicol were quantitated by radioanalytic imagining (AMBIS) and degree of acetylation was calculated. The picograms of CAT enzyme present in each tissue sample was calculated by comparison of experimental values to a known standard (5 Prime 3 Prime, West Chester, Pa.).

Analysis of β-galactosidase Activity

Injected tissues were fixed in paraformaldehyde prior to incubation in an X-Gal staining solution (19). Tissues were sectioned, counterstained with neutral fast red and examined under the microscope for evidence of β-galactosidase activity.

RESULTS

CAT Expression in Living Animals

CAT activity was measured in skin, muscle, fat, and mammary tissue following jet injection of the HCMVIE1 CAT expression vectors at the skin surface (Table 1). In the mouse, activity was detected muscle tissue 2–3 mm distant from the site of injection, the skin surface. In the sheep, mammary gland cells 1 to 3 cm distant from the site of injection, the skin, were successfully transfected (Table 1). CAT activity could not be detected in all samples, most likely secondary to a combination of variability in transfection efficiency and sampling error.

CAT Expression in Cultured Mammary Glands

The HCMVIE1 CAT expression vector was active following jet injection into both mouse and sheep mammary gland cultured in vitro. The WAP CAT vector was expressed in the mouse mammary gland but was not tested in the sheep mammary gland (Table 1).

β-galactosidase Expression in Living Animals

β-galactosidase activity was detected in mouse skin and mammary gland following jet injection of a β-galactosidase expression vector at the skin surface.

Morbidity and Mortality from Jet Injection

There was no significant morbidity in the sheep following jet injection and they continued to lactate after the procedure. Resolving hematomas were found at 2 out of 6 cites of injection at the time of autopsy. The only morbidity in the male mice was occasional transient bleeding. No evidence of injury was found at the time of autopsy 48 hours later.

There were 4 mortalities out of the 15 pregnant mice injected into the skin overlying the mammary gland. Three immediately hemorrhaged extensively following injection and were killed by cervical dislocation. One mouse died 36 hours following injection. An extensive abdominal hematoma was found at autopsy.

All of the remaining mice appeared to be healthy during the 48 hours following injection. None had evidence of hemorrhage or extensive tissue damage at the time of autopsy. A 0.5 mm diameter path of injection through the skin, mammary gland and peritoneum could be traced in two of the mice.

Table 1 below illustrates the results of the above tests.

TABLE 1

| Species | Gene Construct | Tissue | Total number | Number positive | CAT enzyme, range (pg/mg protein) |
|---|---|---|---|---|---|
| Mice | HOMVIE1 | Skin | 3 | 1 | 2.2 |
| | | Muscle | 3 | 3 | 1.0–8.2 |
| | | Mammary gland | 3 | 2 | 1.4–1.9 |
| | | Mammary gland culture | 3 | 3 | 43.6–256.0 |
| | WAP-CAT | Mammary gland | 1 | 0 | <0.5 |
| | | Mammary gland culture | 2 | 2 | 38.8–43.6 |
| Sheep | HOMVIE1 | Skin | 7 | 2 | 0.6–2.0 |
| | | Fat | 7 | 3 | 2.4–228.0 |
| | | Mammary gland | 7 | 4 | 0.6–185.0 |
| | | Mammary gland culture | 2 | 2 | 0.7–1.5 |

As is clear from the above described experiments, their results demonstrate that differentiated tissues of living animals and isolated organs can be transfected with DNA using a jet injection technique. The use of jet injection for introducing DNA into somatic tissues may have advantages over transfection by particle bombardment. First, no metal needs to be introduced with the DNA and second, jet injection can be used to transfect cells millimeters to centimeters beneath the skin surface while particle bombardment is reported to be limited to the first 8–20 cell layers; (Klein, T. M., Arentzen, R., Lewis, P. A., and Fitzpatrick-McElligott, S. (1992) *BIO/TECHNOLOGY* 10, 286–291).

Needle injection of DNA into tissue in either a sucrose or lipofection solution are alternative methods. However, we were unable to detect CAT activity in sheep mammary gland following needle injection of DNA in TE (data not shown).

Suspending gene constructs in solutions which enhance cellular uptake of DNA may improve the efficiency of jet injection.

Important features of jet injection are the ability to inject through intact skin, and the minimal morbidity and pain associated with each injection. These features would permit the practical use of multiple injections to improve transfection efficiency. Jet injection can be used to transiently express genes controlled by differentiation specific factors. The WAP promoter is inactive in virtually all cell culture lines; (Doppler, W., Villunger, A., Jennewein, P., Brduscha, K., Groner, B., and Ball, R. K. (1991) *Mol. Endocrinol.* 5, 1624–1632) and the use of transgenic animals has been the predominant means to study the activity of the promoter; (Hennighausen, L. (1992) *J. Cell. Biochem.*, in press). Jet injection may offer a less costly and time-consuming method to analyze regulatory elements. The same approach may be applied to other tissues as well.

In summary, DNA can be introduced into differentiated somatic cells by jet injection. Modifications to the technique may improve transfection efficiency. The use of replicating vectors could increase expression levels and enhance integration of the expression vector; (Niwa, H., Yamamura, K., and Mizazaki, J. (1991) *Gene* 108, 193–200). The technique may be useful for genetic immunization, to deliver somatic gene replacement treatment and to target gene therapy to tumor cells using toxin or apoptosis genes.

DETAILED DESCRIPTION OF THE DRAWINGS

FIG. 1

Figure 1:
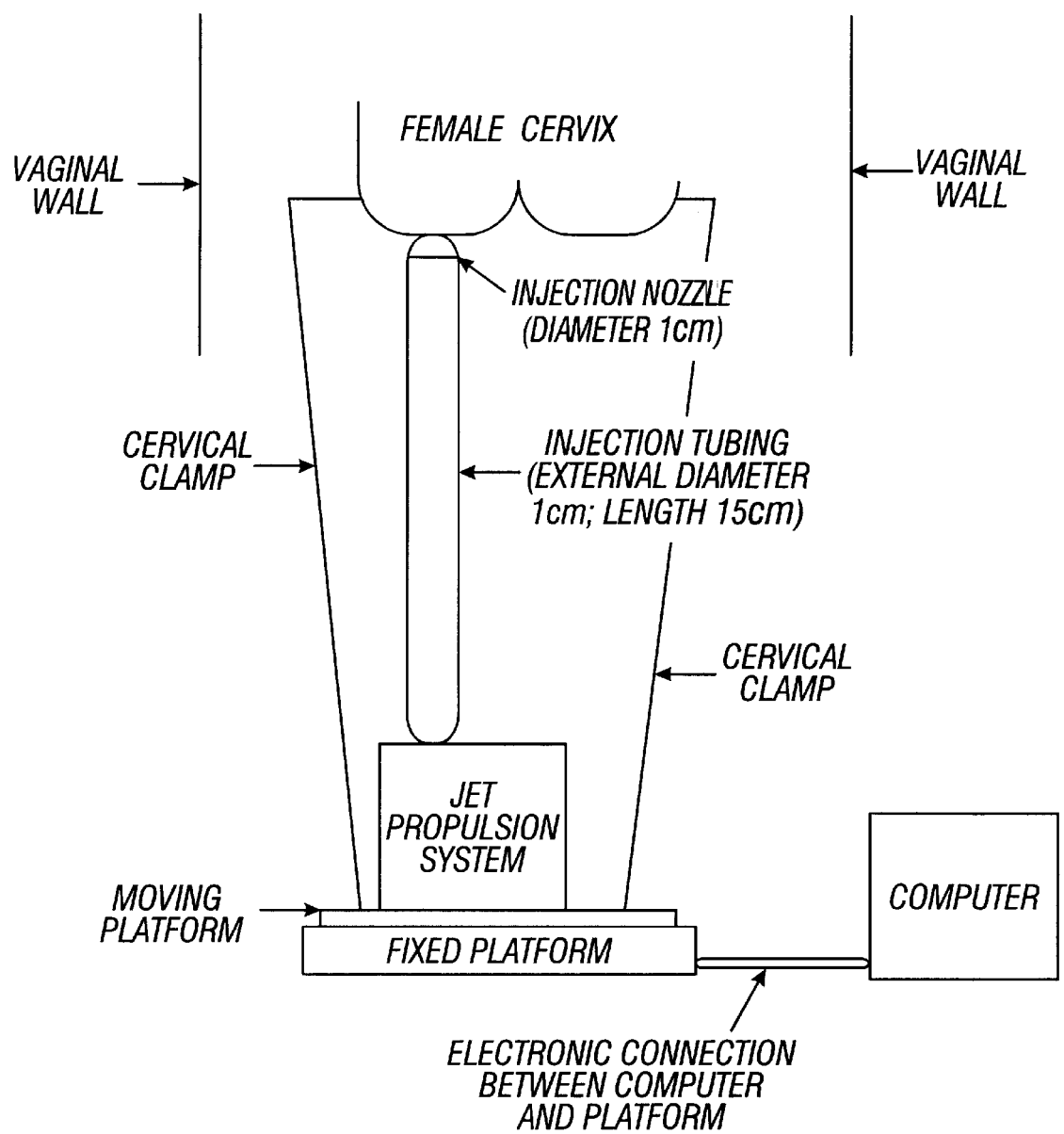
FIG. 1 is a diagram showing an improved jet injection device for injection of DNA into the human female cervix.

FIG. 1 is a diagram showing an improved jet injection device for injection of DNA into the human female cervix. As shown in FIG. 1, this improved jet injection device for injection of the human female cervix consists of a jet injection nozzle which is small enough to position on the human female cervix (which is located within the vagina). FIG. 1 shows a diagram of the vagina at the location of the cervix, the cervix, the injection device, the supporting system for the injection device, and a cervical clamp or clamps holding the injection device in position in the vagina.

The injection device is shown by FIG. 1 to have an injection nozzle contacting the cervix, the injection tubing connecting the injection nozzle and the jet propulsion system, the jet propulsion system, a fixed platform for positioning the nozzle, a computer nozzle is located at the end of a length of injection tubing sufficient to position the injection nozzle on the surface of the cervix, with the jet propulsion system located outside the body. The jet propulsion system is similar to that of the well-known Ped-O-Jet system, which is readily adapted to fit the remainder of the device which is shown in FIG. 1. It is connected to the injection nozzle portion by injection tubing.

The device nozzle, as shown in FIG. 1, is held in position at the cervix by cervical clamps. The nozzle is moved over the entire surface of the cervix by moving a platform which is located outside the body, which platform guides the nozzle. The movements of the platform are controlled by computer to insure that small movements will be made (approximately four millimeter movements are optimal) and the entire cervical surface is covered with injections. As an alternative, a manually driven device can be substituted for the computer.

The dimensions for the device and its components as shown in FIG. 1 are for illustration purposes only and can be readily adapted to other acceptable parameters by those having routine skill by us of routine experimentation to optimize the device in a particular instance.

FIG. 2

Figure 2:
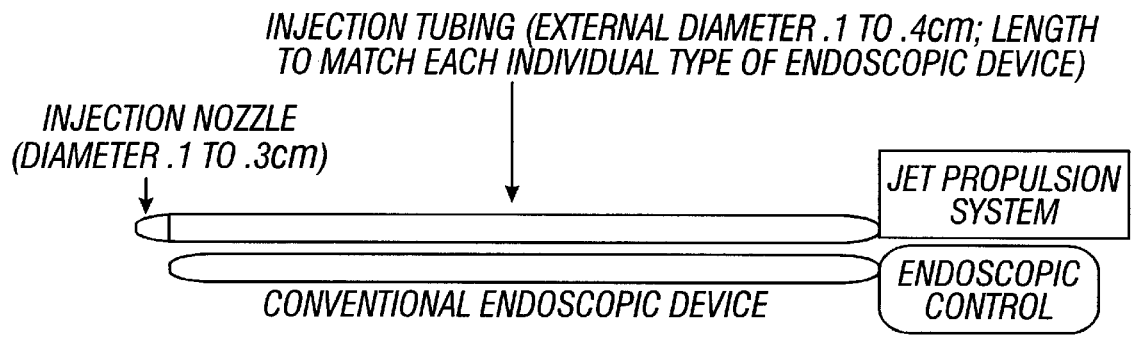
FIG. 2 is a diagram showing an improved jet injection device for injection of DNA into living tissue using an endoscopic device.

FIG. 2 is a diagram showing an improved jet injection device for injection of DNA into living tissue using an endoscopic device. This Figure shows an endoscopic device with its controls, an injection nozzle, a jet propulsion system (generally as described in the discussion of FIG. 1, above), and an injection tubing apparatus connecting the injection nozzle with the jet propulsion system. This Figure shows the injection device system separate from the endoscopic device, but combining the two pieces of apparatus together in a single device is an optional embodiment of the present invention.

The improved jet injection device for injection of living tissue using an endoscopic device may be used in endoscopy, bronchoscopy, cystoscopy, colonoscopy, laparoscope, or other similar procedures using a type of endoscopic device. It works generally in the same manner as discussed in the description of FIG. 1 above, but the endoscopic device is used to view the injection site and aid in the position of the injection nozzle portion of the injection device.

The endoscopic injection device is coupled to conventional endoscopic technology. The endoscope is used to visualize the tissue to be injected and to position the jet injection device at that sight. The jet injection nozzle and tubing is made small enough to enter the appropriate body orifice for each individual endoscopic device.

The dimensions for the device and its components as shown in FIG. 2 are for illustration purposes only and can be readily adapted to other acceptable parameters by those having routine skill using only routine experimentation to optimize the device in a particular instance.

FIG. 3

FIG. 3 is a diagram showing an improved jet injection nozzle for the deep injection of DNA into tissues. FIG. 3 shows two embodiments of the deep injection nozzle. As shown in this Figure the injection nozzle may have one or more ports on the nozzle, which are located at the tip, along the transverse axis of the nozzle, or both at the tip and along the transverse axis of the nozzle. Injection device 1 of FIG. 3 shows a single deep tissue injection nozzle, whereas device 2 of FIG. 3 shows multiple deep injection nozzles (e.g., two injection nozzles). More than two deep injection nozzles may be used with device 2, if required in a particular instance to obtain optimal results. The propulsion system and tubing connecting the nozzle (or nozzles) with the propulsion system as essentially as described generally in FIG. 3.

The improved jet injection nozzles of FIG. 3, for deep injection of tissue, are designed to be able to deliver a jet injection to a tissue internally. The needle injection device is inserted into a tissue at the required depth. The injection is then performed. Two types of needle injections can be used. Optionally the deep injection device can also have a computer guided or manually guided means to set the exact depth at which the nozzle is inserted into the subject tissue.

As shown in FIG. 3, and discussed above a first type of device delivers the injection through a single port (device 1), and a second type of device delivers the injection through multiple ports, i.e. two or more injection ports, (device 2). The diagram in FIG. 3 shows one port at the end of the needle and one port on each side on the multiple port injection nozzle. Additional ports may be added as needed for particular tissues to inject at a single level in the tissue or at multiple levels throughout the tissue as required for optimal results.

The diameter of each of the needle-like deep injection devices, as shown in FIG. 3, is varied for each type of tissue to obtain optimal results. The range is usually between 12 and 18 gauge, which is a large diameter needle. An optimal range for the diameter is readily determined by one of routine skill using only routine experimentation until optimal results are obtained.

The dimensions for each of the devices and its respective components, as shown in FIG. 3, are for illustration purposes only and can be readily adapted to other acceptable parameters by those having routine skill using only of routine experimentation to optimize the device in a particular instance.

Moreover, the concepts shown in each of FIGS. 1 through 3 may be combined with each other or with the concepts described in other devices described in this application. Adaptations can be readily made to obtain optimal results in a particular situation.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

What is claimed is:

1. A method for obtaining gene expression in somatic cells of a subject comprising:

a) administering a plasmid expression vector containing a gene encoding a polypeptide or peptide to cells of the subject in vivo using a jet injector; and b) expressing the gene in the cells, thereby obtaining gene expression.

2. The method according to claim 1, wherein said plasmid expression vector comprises DNA sequences selected from the group consisting of a DNA sequence containing enhancer/promotor or other regulatory elements, a DNA sequence which can be transcribed into an RNA which RNA can be (a) translated into a protein, (b) includes a transcriptional termination signal, and (c) may include coding sequences for a signal peptide which allows a protein to be exported from the cell, a DNA sequence which provides for incorporation of a gene into the genome, a DNA sequence which replicates in eukaryotic cells, and a plasmid sequence which allows DNA replication in prokaryotic cells.

3. The method according to claim 2, wherein the enhancer/promoter sequence is a naturally occurring element.

4. The method according to claim 3, wherein the enhancer/promoter sequence is the HCMVIE1 promoter/enhancer or the enhancer/promoter sequences constructed using DNA elements which mediate binding by transcription factors to express in cells administered the plasmid expression vector.

5. The method according to claim 2, wherein the enhancer/promoter is comprised of a generic TATA box and binding sites for the E2 transcription factor and said enhancer/promoter is a papillomavirus enhancer/promoter, wherein said enhancer/promoter is functional in cells that express the DNA encoding E2 protein from papillomavirus.

6. The method of claim 1, wherein said plasmid expression vector comprises an enhancer/promoter and a DNA sequence selected from the group consisting of human cytomegalovirus immediate early gene 1 and whey acidic protein promoter sequence.

7. The method of claim 1, wherein said plasmid expression vector comprises pairs of DNA sequences in operable linkage selected from the group consisting of human cytomegalovirus immediate early gene 1 and chloramphenicol acetyl transferase gene; whey acidic protein promoter sequence and chloramphenicol acetyl transferase gene; and human cytomegalovirus immediate early gene 1 and β-galactosidase gene.

8. The method of claim 1, wherein said plasmid expression vector is expressed in a living organism at about 1 to about 3 cm. distance along the direction of the path of the injection.

9. The method of claim 1, wherein said plasmid expression vector comprises supercoiled DNA of 1 microgram/microliter in 1 mM TRIS-.1 mM EDTA and is administered in volumes between 100 microliters and 500 microliters per injection.

10. The method according to claim 1, wherein said polypeptide or peptide expressed by said expression vector confers immunity to said subject.

11. A method of inducing an immune response in a subject using a jet injector comprising:

a) delivering via the jet injector an effective amount of a plasmid expression vector encoding a polypeptide or peptide to transform differentiated somatic cells of the subject; and b) expressing the gene in the cells, wherein the polypetide or peptide expressed from said plasmid expression vector confer immunity to the subject.

12. The method as in claim 1 or 11, wherein the cells are selected from the group consisting of epithelium, muscle, fat and mammary tissue of the subject.

* * * * *